(12) United States Patent
Dieckgraefe

(10) Patent No.: US 6,228,585 B1
(45) Date of Patent: May 8, 2001

(54) GENE MARKERS FOR CHRONIC MUCOSAL INJURY

(75) Inventor: Brian K. Dieckgraefe, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 09/146,969

(22) Filed: Sep. 4, 1998

(51) Int. Cl.[7] .............................. C12Q 1/68; C12P 19/34
(52) U.S. Cl. ................................ 435/6; 435/91.2
(58) Field of Search ........................ 435/6, 91.2

(56) References Cited

FOREIGN PATENT DOCUMENTS

WO 97 25445   7/1997  (WO).
WO 98 00561   1/1998  (WO).
WO 98 41633   9/1998  (WO).

OTHER PUBLICATIONS

Fukui et al. Gastroenterology (1998) 115:1483–1493.*
McKie et al. Clinical Science (1996) 91:213–218.*
Kawanami et al. J. Gastroenterol. (1997) 32:12–18.*
Baroli et al. J. Clin. Endocrin. Metab. (1998) 83(11): 4041–4046.*
Juan Lucio Iovanna et al. "Serum Levels of Pancreatitis–Associated Protein as Indicators of the Course of Acute Pancreatitis" Gastroenterology 1994:106:728–734.
Yoshiharu Motoo et al. "Expression of Pancreatitis–Associated Protein (PAP) mRNA in Gastrointestinal Cancers" International Journal of Pancreatology, vol. 23, No. 1, 11–16, Feb. 1998.
Tetsuo Hayakawa et al. "Serum Pancreatic Stone Protein in Pancreatic Diseases" International Journal of Pancreatology, vol. 13, No. 2, 97–103, Apr. 1993.
A. Carroccio et al. "Pancreatitis–Associated Protein in Patients with Celiac Disease: Serum Levels and Immunocytochemical Localization in Small Intestine" Digestion 1997:58–98–103.

Yoshitake Satomura et al. "Measurement of serum PSP/reg–protein concentration in various diseases with a newly developed enzyme–linked immunonosorbent assay" J. Gastroenterol 1995; 30:643–650.

Watanabe et al. "Complete Nucleotide Sequence of Human REG Gene and its Expression in Normal and tumoral Tissues the REG Protein, Pancreatic Stone Protein, and Pancreatic Thread Protein are One and the Same Product of the Gene" Journal of Biological Chemistry, U.S., American Society of Biological Chemists, vol. 265, No. 13, May 5, 1990 pp. 7432–7439.

Dieckgraefe et al. "Characterization of mucosal gene expression in inflammatory bowel disease by direct hybridization to massively parallel oligonucleotide arrays" Gastroenterology Apr. 15, 1998 vol. 114, No. 4, Part 2 pp. A964.

Dieckgraefe et al. "Expression of the regenerating gene family in inflammatory bowel disease: Potential role as an injury–induced tissue mitogen" Gastroenterology, Apr. 1999 vol. 116, No. 4 Part 2, pp. A601.

* cited by examiner

Primary Examiner—Lisa B. Arthur
(74) Attorney, Agent, or Firm—Banner & Witcoff LTD

(57) ABSTRACT

The invention provides gene markers for chronic mucosal injury and ulcerative colitis. Expression products of the REG gene family can be used to detect the presence of chronic mucosal injury in a body sample of a human. The expression products of a gene represented by a Hs.111244 polynucleotide can be used to detect ulcerative colitis in a body sample of a human. Further, these markers can be used to differentiate humans with chronic mucosal injury from humans with common acute inflammatory colon disorder, common non-inflammatory benign colon disorder, and healthy colons. The degree of injury to the colon from chronic mucosal injury can be determined and the efficacy of therapy for chronic mucosal injury can be monitored. A method of screening compounds for anti-chronic mucosal injury and anti-ulcerative activity is also provided by these gene markers.

7 Claims, 2 Drawing Sheets pM RNA concentration

SEQUENCE LISTING

<160> NUMBER OF SEQ ID NOS: 5

<210> SEQ ID NO 1
<211> LENGTH: 777
<212> TYPE: DNA
<213> ORGANISM: Homo sapiens

<400> SEQUENCE: 1

| | | | | | |
|---|---|---|---|---|---|
| ttcttcaaac | cctcctcttc | cctgtgttct | cctacagaga | ttgctgattt | ctccttaagc | 60 |
| aagagattca | ctgccgctaa | gcatggctca | gaccaactcg | ttcttcatgc | tgatctcctc | 120 |
| cctgatgttc | ctgtctctga | gccaaggcca | agaggcccag | acagagttgc | ccaggcccg | 180 |
| gatcagctgc | ccagaaggca | ccaatgccta | tcgctcctac | tgctactact | ttaatgaaga | 240 |
| ccgtgagacc | tggttgatg | cagatctcta | ttgccagaac | atgaattcgg | gcaacctggt | 300 |
| gtctgtgctc | acccaggccg | agggtgcctt | tgtggcctca | ctgattaagg | agagtggcac | 360 |
| tgatgacttc | aatgtctgga | ttggcctcca | tgaccccaaa | agaaccgcc | gctggcactg | 420 |
| gagcagtggg | tccctggtct | cctacaagtc | ctggggcatt | ggagcccaa | gcagtgttaa | 480 |
| tcctggctac | tgtgtgagcc | tgacctcaag | cacaggattc | cagaaatgga | aggatgtgcc | 540 |
| ttgtgaagac | aagttctcct | ttgtatgcaa | gttcaaaaac | tagaggcagc | tggaaaatac | 600 |
| atgtctagaa | ctgatccagc | aattacaacg | gagtcaaaaa | ttaaaccgga | ccatctctcc | 660 |
| aactcaactc | aacctggaca | ctctcttctc | tgctgagttt | gccttgttaa | tcttcaatag | 720 |
| ttttacctac | cccagtcttt | ggaaccctaa | ataataaaaa | taaacatgtt | ttccact | 777 |

<210> SEQ ID NO 2
<211> LENGTH: 798
<212> TYPE: DNA
<213> ORGANISM: Homo sapiens

<400> SEQUENCE: 2

| | | | | | |
|---|---|---|---|---|---|
| cgggagagtg | actcctgatt | gcctcctcaa | gtcgcagaca | ctatgctgcc | tcccatggcc | 60 |
| ctgcccagtg | tatcttggat | gctgctttcc | tgcctcatgc | tgctgtctca | ggttcaaggt | 120 |
| gaagaacccc | agagggaact | gccctctgca | cggatccgct | gtcccaaagg | ctccaaggcc | 180 |
| tatggctccc | actgctatgc | cttgtttttg | tcaccaaaat | cctggacaga | tgcagatctg | 240 |
| gcctgccaga | agcggccctc | tggaaacctg | gtgtctgtgc | tcagtggggc | tgagggatcc | 300 |
| ttcgtgtcct | ccctggtgaa | gagcattggt | aacagctact | catacgtctg | gattgggctc | 360 |
| catgacccca | cagggcac | cgagcccaat | ggagaaggtt | gggagtggag | tagcagtgat | 420 |
| gtgatgaatt | actttgcatg | ggagagaaat | ccctccacca | tctcaagccc | cggccactgt | 480 |
| gcgagcctgt | cgagaagcac | agcatttctg | aggtggaaag | attataactg | taatgtgagg | 540 |
| ttaccctatg | tctgcaaagt | tcactgacta | gtgcaggagg | gaagtcagca | gcctgtgttt | 600 |
| ggtgtgcaac | tcatcatggg | catgagacca | gtgtgaggac | tcaccctgga | agagaatatt | 660 |
| cgcttaattc | ccccaacctg | accacctcat | tcttatcttt | cttctgtttc | ttcctccccg | 720 |
| ctagtcattt | cagtctcttc | attttgtcat | acggcctaag | gctttaaaga | gcaataaaat | 780 |
| ttttagtctg | caaaaaaa | | | | | 798 |

<210> SEQ ID NO 3
<211> LENGTH: 586
<212> TYPE: DNA
<213> ORGANISM: Homo sapiens -continued

<400> SEQUENCE: 3

```
ttcccatgac cctctgtagg atgtcttgga tgctgctttc ctgcctgatg ttcctttctt    60
gggtggaagg tgaagaatct caaaagaaac tgccttcttc acgtataacc tgtcctcaag   120
gctctgtagc ctatgggtcc tattgctatt cactgatttt gataccacag acctggtcta   180
atgcagaact atcctgccag atgcatttct caggacacct ggcatttctt ctcagtactg   240
gtgaaattac cttcgtgtcc tcccttgtga agaacagttt gacggcctac cagtacatct   300
ggattggact ccatgatccc tcacatggta cactacccaa cggaagtgga tggaagtgga   360
gcagttccaa tgtgctgacc ttctataact gggagaggaa cccctctatt gctgctgacc   420
gtggttattg tgcagttttg tctcagaaat caggttttca gaagtggaga gattttaatt   480
gtgaaaatga gcttccctat atctgcaaat tcaaggtcta gggcagttct aatttcaaca   540
gcttgaaaat attatgaagc tcacatggac aaggaagcaa gtatga              586
```

<210> SEQ ID NO 4
<211> LENGTH: 3411
<212> TYPE: DNA
<213> ORGANISM: Homo sapiens

<400> SEQUENCE: 4

```
aggaagggca aagctcaaca tcaacttgga cagtttgcca acctgtttgt ggtaagttga    60
tgtcatttgt gaccactcct aatgtgtgcc accaataagc tattcctgat gccagaatct   120
cttactgtca gtgccctctg taggccttct gatccttact ccttgctcca cccattgttt   180
atatcatgta gttctctctc agaccctgat ataaagctcc tactctgtct gacctgacaa   240
gccacctcaa gtggacaagg cacttaccaa caggtaaagg ggcattacag gagaagagca   300
tgtctaacgt gggatttct cttttcattt tgaggtagat acaggtgat tttctgaata   360
aaagatccca gtagtaatga aacttaagca agaccaaagc tgatttcggg taatttggcc   420
tctgttatcc ccaaaccaaa agagaaatat ctgggagtgt agctatctca gtggaccttt   480
ctgctcacag gaattcagag aggagaggat gttagaaaga taacaggtgc tctgctctct   540
tcttcaaacc ctcttccctg tgttctccta cagagattgc tgatttgctc cttaagcaag   600
agattcactg ccgctaagca tggctcagac caactcgttc ttcatgctga tctcctccct   660
gatgttcctg tctctgagcc aaggtgagat ttttcccccac acttcccaca accccaactc   720
tgaattcttc cctccatcct catgtataag gttcacttga aaaaaagcag agtcaacatc   780
agggttttt tatgttgttc agtgatcatt atggctgatt ttatcccatt caaaacacc   840
ctcaccttca ttcatgggtt tgagacagaa tttaatagga ccacttatag gtgaccattg   900
tggttgagtt tatctgattg aatctatatg cgatggcagt ttgggggatg ttttatgta    960
gtcattgcta ggatgagagc taaggcaaac gtgtgcaggg aaaccgagag aaacttgaga  1020
aaggaggaag cctgggtctt taaaggcaga agcctcagcc tcagaattaa ggaaaacga   1080
gaactcattt atttagccta ttcattgtga gctcttgtct tgagcagagg aaactagaga  1140
gaaaagagat aggatgcagg agggcagaag tgagcaatcg ccccagtatt cactgtatcc  1200
atatgttctt ataaggacac caagaagccc ctattcacct tccagccttt tccttgccct  1260
gagattcttt cttagttatc tccttttttt tttccccagg ccaggagtcc cagacagagc  1320
tgcctaatcc ccgaatcagc tgcccagaag gcaccaatgc ctatcgctcc tactgctact  1380
actttaatga agaccctgag acctgggttg atgcagatgt gagtgaggag agcagcaggg  1440
```

-continued

```
gaaggaggc ttatgaaggt agaggcagct gctaatttgc agtgtgttct gtggctgcaa      1500
tgagataaga ttgatcccct ccctattcca ccactggtcc aaaacttccc aatctacttt      1560
atcccatcat ttgacacatt cccagcacag agatgctggt ggtcagtgac agcatcatca      1620
gggacatttc tgtgctgtcc ttttctgtt acatcctctg gaaggtctca gtatatccct      1680
cacaccttcc ttctccactg agtgctccat tttcttctcc aacagctcta ttgccagaac      1740
atgaattcag gcaacctggt gtctgtgctc acccaggcgg agggtgcctt cgtggcctca      1800
ctgattaagg agagtagcac tgatgacagc aatgtctgga ttggcctcca tgacccaaaa      1860
aaggtcagtc tgcagccacc tctatctcct tataaacatt tttgagaggt aagagggacg      1920
tttaaggtct ggcaccgcaa tcaccaactt ttatctttt gtttgtttaa ataaaagcaa      1980
cctctttata gatcctataa tgtatgagtt gtgaagttca gtgtaggtag ttagagacat      2040
gagctgaagg ctgaatttc tgggctctgg gaattcatgc acccactcat tgtgtctact      2100
tctagaaatg catctttatg tacaacttt tccctatttt gctattgtct gtcttggaag      2160
aggtccctct gtagactata tagaaaatga gtagtggagg agaatctact gctggcattt      2220
gttatacatt ttatacaagt gtataaaact gtacagtata ttatttagtt taacactata      2280
aactaaataa tatatcaaca actactctac agccaatgtt atgctggata tgagagttct      2340
gagattcagg aaaaaaatca gaaaccactc tctgtaatgg gcttttatgg gtctctgtat      2400
caaattctga acacttatta tttgctagaa gaggaggagg aattcggaca ttctagagaa      2460
ggagaagctt agagcaaaag cagaggaaat gatatgatat tcatggtgac aacaatgttt      2520 attcttctg ctataacttg gcctgtttct gagtgtgcac acaggcctgg ttattctatt      2580 gattttgag tgaccatggc ccctgttctg gcccttctcc atctagaacc gccgctggca      2640
ctggagtagt gggtccctgg tctcctacaa gtcctgggac actggatccc cgagcagtgc      2700
taatgctggc tactgtgcaa gcctgacttc atgctcaggt gagaggcaga caatctatcc      2760
acctgttgcc atttccttcc cacttatctc tggggatgaa catgggggact gggatagagg      2820 aaaggtaagc tccttatctg gaaaataaag aagtattcc tctagttttt tgttctgagt      2880
cctaggttga ggaggggcta cactccttct gatcctctat gtctgacact tctcattgta      2940
ctataggatt caagaaatgg aaggatgaat cttgtgagaa gaagttctcc tttgtttgca      3000
agttcaaaaa ctagaggaag ctgaaaaatg gatgtctaga actggtcctg caattactat      3060
gaagtcaaaa attaaactag actatgtctc caactcagtt cagaccatct cctccctaat      3120
gagtttgcat cgctgatctt cagtaccttc acctgtctca gtctctagag ccctgaaaaa      3180 taaaacaaa cttatttta tccagtgttc tgtcttctgc atttgctctt tctacagccc      3240
atgcttgggt ggttggggtg ggaatgattg tcacactcca gagcttgcca tggcccatcc      3300
acttgttaaa accccactca catttatgt atgtcaggct tatgaacatg tggtggcctt      3360
gtttatgaca agataaaaag attaagattt catccacaac acatgttagc a             3411
```

<210> SEQ ID NO 5
<211> LENGTH: 1734
<212> TYPE: DNA
<213> ORGANISM: Homo sapiens

<400> SEQUENCE: 5

```
gcgagcgtgg aactgggacg ggtctgggcg gctctcggtg gttggcacgg gttcgcacac        60
ccattcaagc ggcaggacgc acttgtctta gcagttctcg ctgaccgcgc tagctgcggc       120
ttctacgctc cggcactctg agttcatcag caaacgccct ggcgtctgtc ctcaccatgc       180
```

```
ctagcctttg ggaccgcttc tcgtcgtcgt ccacctcctc ttcgccctcg tccttgcccc    240
gaactcccac cccagatcgg ccgccgcgct cagcctgggg gtcggcgacc cgggaggagg    300
ggtttgaccg ctccacgagc ctggagagct cggactgcga gtccctggac agcagcaaca    360
gtggcttcgg gccggaggaa gacacggctt acctggatgg ggtgtcgttg cccgacttcg    420
agctgctcag tgaccctgag gatgaacact tgtgtgccaa cctgatgcag ctgctgcagg    480
agagcctggc ccaggcgcgg ctgggctctc gacgccctgc gcgcctgctg atgcctagcc    540
agttggtaag ccaggtgggc aaagaactac tgcgcctggc ctacagcgag ccgtgcggcc    600 tgcgggggggc gctgctggac gtctgcgtgg agcagggcaa gagctgccac agcgtgggcc    660
agctggcact cgaccccagc ctggtgccca ccttccagct gaccctcgtg ctgcgcctgg    720
actcacgact ctggcccaag atccaggggc tgtttagctc cgccaactct cccttcctcc    780
ctggcttcag ccagtccctg acgctgagca ctggcttccg agtcatcaag aagaagctgt    840
acagctcgga acagctgctc attgaggagt gttgaacttc aacctgaggg ggccgacagt    900
gccctccaag acagagacga ctgaacttt ggggtggaga ctagaggcag gagctgaggg    960
actgattcct gtggttggaa aactgaggca gccacctaag gtggaggtgg gggaatagtg   1020
tttcccagga agctcattga gttgtgtgcg ggtggctgtg cattggggac acatacccct   1080
cagtactgta gcatgaaaca aaggcttagg ggccaacaag gcttccagct ggatgtgtgt   1140
gtagcatgta ccttattatt tttgttactg acagttaaca gtggtgtgac atccagagag   1200
cagctgggct gctcccgccc cagcccggcc cagggtgaag gaagaggcac gtgctcctca   1260
gagcagccgg agggaggggg gaggtcggag gtcgtggagg tggtttgtgt atcttactgg   1320
tctgaaggga ccaagtgtgt ttgttgtttg ttttgtatct tgttttctg atcggagcat    1380 cactactgac ctgttgtagg cagctatctt acagacgcat gaatgtaaga gtaggaaggg   1440
gtgggtgtca gggatcactt gggatctttg acacttgaaa aattacacct ggcagctgcg   1500
tttaagcctt cccccatcgt gtactgcaga gttgagctgg caggggaggg gctgagaggg   1560
tgggggctgg aacccctccc cgggaggagt gccatctggg tcttccatct agaactgttt   1620
acatgaagat aagatactca ctgttcatga atacacttga tgttcaagta ttaagaccta   1680
tgcaatattt tttacttttc taataaacat gtttgttaaa acaaaaaaaa aaaa          1734
```

GENE MARKERS FOR CHRONIC MUCOSAL INJURY

BACKGROUND OF THE INVENTION

Clinical assessment of disease activity in ulcerative colitis or Crohn's disease is very difficult. Patient symptoms do not necessarily correlate with the inflammatory (disease) activity in the small intestine and colon, leading to educated guesses being used to direct anti-inflammatory therapy. Similar difficulty exists in measuring or testing the efficacy of new therapeutic compounds. Currently the gold standard in diagnosing ulcerative colitis or Crohn's disease is the use of fiberoptic endoscopy coupled with multiple biopsies and pathologic analysis. This very expensive approach requires a skilled specialist and has associated risks, such as risk of sedation, bleeding, and colon perforation. The patient is also subjected to discomfort from the procedure and preparation.

A less invasive and less risky assessment of mucosal disease activity is needed to accurately guide treatment and to provide an objective measure of mucosal injury, both for patients and for use in clinical studies. There is also a need for a simple test to aid in the differentiation of chronic inflammatory disease (UC or CD) from common acute inflammatory disorders or common non-inflammatory benign disorders. There is a further need for a simple method for the differentiation of ulcerative colitis and Crohn's disease because the surgical and medical management for these two diseases is profoundly different.

SUMMARY OF THE INVERSION

It is an object of the invention to provide a method for identifying chronic mucosal injury in a human.

It is another object of the invention to provide a method of determining the degree of injury to the small intestine or colon of a human with chronic mucosal injury.

It is yet another object of the invention to provide a method for monitoring the efficacy of therapy for chronic mucosal injury.

It is a further object of the invention to provide a method of screening compounds for anti-chronic mucosal injury or anti-ulcerative colitis activity.

These and other objects of the invention are provided by one or more of the embodiments described below.

One embodiment of the invention provides a method of diagnosing chronic inflammatory bowel disease. At least one gene expression product of the regenerating (REG) gene family is detected in a body sample of a human who is suspected of having chronic inflammatory bowel disease. The human is identified as having chronic inflammatory bowel disease if the gene expression product is detected.

A further embodiment of the invention provides a method to aid in the differentiation of chronic mucosal injury from common acute inflammatory colon disorder and common non-inflammatory benign colon disorder in a human with symptoms of bowel disease. The amount of at least one gene expression product of the REG gene family in a body sample of a first human who is suspected of having bowel disease, is compared with the amount of the gene expression product in a body sample of a second human who is healthy. The first human is identified as having chronic mucosal injury if the body sample of the first human contains more of the gene expression product than the body sample of the second human.

Another embodiment of the invention provides a method to determine degree of injury to small intestine or colon tissue of a human with chronic mucosal injury. A quantity of a gene expression product of the REG gene family in a body sample of a human having chronic mucosal injury is determined. The amount is correlated with the degree of injury to the small intestine or colon.

Still another embodiment of the invention provides a method of monitoring the efficacy of therapy for chronic mucosal injury in a human body sample. At least one gene expression product of the REG gene family is quantitated in a body sample of a human who has been subjected to therapy for chronic mucosal injury. The quantity of the expression product in the sample is compared to the quantity of the gene expression product in a matched body sample of the human at an earlier time. A reduction in the quantity of the gene expression product after therapy is an index of efficacy of the therapy.

Another embodiment of the invention provides a method of screening compounds for anti-chronic mucosal injury activity. A colonic cell expressing a gene which is a member of the REG gene family is contacted with a test compound. The expression of the REG gene is quantitated. A test compound which decreases expression of the gene is identified as a potential compound for treating chronic mucosal injury.

A further embodiment of the invention provides a method of diagnosing ulcerative colitis. An mRNA which is expressed by a gene represented by a Hs.111244 polynucleotide is detected in a body sample of a first human who is suspected of having ulcerative colitis. The human is identified as having ulcerative colitis if the mRNA is detected.

Still another embodiment of the invention provides a method to aid in the differentiation of ulcerative colitis from common acute inflammatory colon disorder, common non-inflammatory benign colon disorder, and Crohn's disease in a human with symptoms of bowel disease. The amount of mRNA which is expressed by a gene represented by a Hs.111244 polynucleotide in a body sample of a first human suspected of having bowel disease is compared with the amount of the mRNA in a comparable body sample of a second human who is healthy. A body sample of the first human which contains more of the mRNA than the body sample of the second human identifies the first human as having ulcerative colitis.

Another embodiment of the invention provides a method to determine the degree of injury to small intestine or colon tissue of a human with ulcerative colitis. A quantity of an mRNA which is expressed by a gene represented by a Hs.111244 polynucleotide in a body sample of a first human having ulcerative colitis is determined. The quantity of the mRNA is correlated with the degree of injury to the small intestine or colon.

Even another embodiment of the invention provides a method of monitoring the efficacy of therapy for ulcerative colitis in a human body sample. An mRNA which is expressed by a gene represented by a Hs.111244 polynucleotide is quantitated in a body sample of a human who has been subjected to therapy for ulcerative colitis. The quantity of the mRNA in the sample is compared to the quantity of the mRNA in a matched body sample of the human at an earlier time. A reduction in the quantity of the mRNA after therapy is an index of efficacy of the therapy.

Still another embodiment of the invention provides a method of screening compounds for anti-ulcerative colitis activity. A colonic cell expressing an mRNA which is expressed by a gene represented by a Hs.111244 polynucleotide is contacted with a test compound. The expression of the mRNA by the cell is quantitated. A test compound which decreases expression of the mRNA is identified as a potential compound for treating ulcerative colitis.

DETAILED DESCRIPTION OF THE PREFERRED EMBODIMENTS

Figures 1, 2:
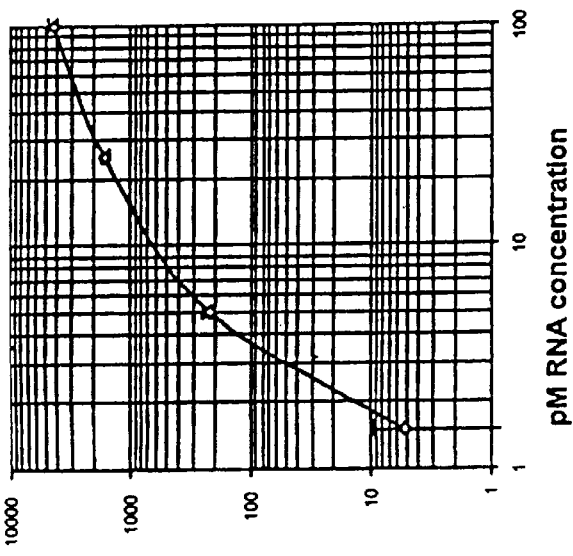
FIG. 1 demonstrates the hybridization signal of spiked controls. The fluorescence intensity for different levels of gene expression was standardized by spiking a known amount of control genes.
FIG. 2 demonstrates the expression of PSP, PAP, and REGH in inflammatory bowel disease.

The inventor has discovered that chronic mucosal injury can be diagnosed by detecting expression levels of the REG gene family and a gene represented by a Hs.111244 polynucleotide in a human body sample. The members of the REG gene family have been found to be strongly expressed in regions of the colon involved with chronic mucosal injury and in the small intestine and colon of humans with Crohn's disease. Additionally, a gene represented by the Hs.111244 polynucleotide is strongly expressed in the colon of humans with ulcerative colitis. Such strong expression is both surprising and useful because the REG gene family and the gene represented by the Hs.111244 polynucleotide are not expressed, or are expressed at low levels, in healthy small intestine and colon tissue. Further, the expression products of the REG gene family and the gene represented by the Hs.111244 polynucleotide can be detected in the serum of humans with chronic mucosal injury and ulcerative colitis, respectively.

Chronic mucosal injury can be caused by inflammatory bowel diseases such as ulcerative colitis and Crohn's disease. Crohn's disease affects both the small intestine and the colon. Chronic mucosal injury can further be caused by immunodeficiencies, such as chronic granulamatous disease and transplantation rejection, and infections, such as mycobacteria.

At the present time, the human regenerating (REG) gene family is known to contain four genes: pancreatic stone protein (PSP) (the protein is also known as thread protein, lithostathine, and Reg) as shown in SEQ ID NO:1, pancreatitis-associatedprotein (PAP) as shown in SEQ ID NO:2, human pancreatic beta cell growthfactor, also known as (INGAP), as shown in SEQ ID NO:3, and regenerating gene homologue (REGH) as shown in SEQ ID NO:4. In normal circumstances, these genes are regionally expressed in low amounts in the small bowel and pancreatic epithelium. Healthy colonic mucosa and small intestine has little or no expression of the REG gene family. Ulcerative colitis, Crohn's disease, or other chronic mucosal injury leads to high levels of REG gene expression in the colonic mucosal or small intestine or both. This expression of the members of the REG gene family correlates with the degree of histopathological injury, and is not seen in the setting of acute self-limited colonic inflammation or common non-inflammatory benign colon disorders.

The nucleic acid sequence of the expressed sequence tag (EST) Hs.111244 is shown in SEQ ID NO:5. The nucleic acid sequence of Hs.111244 has been newly determined and represents a more complete sequence of Hs.111244 than has been previously published. This nucleic acid sequence is referred to herein as the Hs.111244 polynucleotide. The gene represented by the expressed sequence tag (EST) Hs.111244, is not expressed or is expressed at low levels in the healthy colon mucosa, acute self-limited colonic inflammation or common non-inflammatory benign colon disorders, or mucosa affected by Crohn's disease. However, the gene represented by the Hs.111244 polynucleotide is expressed at high levels in colonic mucosa affected by ulcerative colitis.

In humans who have been diagnosed with a bowel disease, detection of levels of at least one gene expression product of the REG gene family in a body sample can be used to diagnose or prognose chronic mucosal injury or to monitor treatment of chronic mucosal injury. The body sample is obtained from a human and can be, for example, a tumor, a solid tissue such as colon or small intestine tissue, or a fluid sample such as blood, serum, or plasma. The human from whom the body sample is obtained can be apparently healthy or can already be identified as having chronic mucosal injury. A comparable body sample is a body sample obtained from a second human which is the same type of body sample as obtained from a first human. A matched body sample is a body sample obtained from the first human at an earlier time which is the same type of body sample from the first human obtained at a later time.

Expression products of the REG gene family can be detected in a body sample. Detection of the expression products in a human's body sample indicates the presence of chronic mucosal injury in the human. In one embodiment, the body sample is assayed for the presence of at least one REG gene family protein. A REG gene family protein or polypeptide, can be detected using, for example, anti-REG gene family-specific antibodies. The antibodies can be labeled, for example, with a radioactive, fluorescent, biotinylated, or enzymatic tag and detected directly, or can be detected using indirect immunochemical methods, using a labeled secondary antibody. The presence of REG gene family protein or polypeptides can be assayed, for example, in tissue sections by immunocytochemistry, or in lysates, using Western blotting, as is known in the art. Further, REG gene family proteins or polypeptides can be assayed by immunoprecipitation assay, enzyme-linked immunoabsorbant assay, quantitative antigen capture-based immunoassay, and radioimmunoassay.

The level of at least one REG gene family protein or polypeptide in a body sample of a human suspected of having a chronic mucosal injury can be compared with the level of the protein or polypeptide in a healthy body sample. The level of a REG gene family protein or polypeptide in a body sample of a human suspected of having chronic mucosal injury can be determined using antibodies specific for the REG gene family protein or polypeptide. The level of the REG gene family protein or polypeptide in a healthy body sample can also be determined. The two levels are compared to each other and a higher level of the REG gene family protein or polypeptide in the suspect human's body sample as compared to the healthy human's body sample indicates the presence of chronic mucosal injury in the suspect human. Preferably, the increased level of the REG gene family protein in the suspect sample is at least 25%, 50%, 100%, 150%, 200% or 250% higher than in the healthy body sample.

Alternatively, the presence of mRNA expressed from at least one member of the REG gene family or mRNA expressed from the gene represented by the Hs.111244 polynucleotide can be detected in a body sample. Detection of mRNA expressed from at least one member of the REG gene family in a body sample of a human indicates the presence of chronic mucosal injury in the human. Detection of mRNA which is expressed by a Hs.111244 polynucleotide in a body sample of a human suspected of having bowel disease indicates the presence of ulcerative colitis in the human.

mRNA expressed from the REG gene family or the gene represented by a Hs.111244 polynucleotide can be detected by any means know in the art. For example, one can use in situ hybridization in tissue sections or Northern blots containing poly $A^+$mRNA. Other techniques such as high density DNA array hybridization, ribonuclease protection assay, and serial analysis of gene expression can also be used. REG gene family- or Hs.111244-specific oligonucleotide probes can be generated using the polynucleotide sequences of the REG gene family or of the gene represented by a Hs.111244 polynucleotide. The probes are preferably at least 12, 14, 16, 18, 20, 22, 24, or 25 nucleotides in length and can be less than 2, 1, 0.5, 0.1, or 0.05 kb in length. The probes, for example, can be synthesized chemically, generated from longer polynucleotides using restriction enzymes, or amplified enzymatically. The probes can be labeled, for example, with a radioactive, biotinylated, or fluorescent tag. A mixture of probes can also be used. Such mixture can contain a plurality of probes which are specific to different REG family genes or specific for the gene represented by the Hs.111244 polynucleotide. Alternatively, each of a plurality of probes can be used separately.

One of skill in the art can readily determine differences in the amount of REG gene family mRNA or a gene represented by a Hs.111244 polynucleotide mRNA transcripts between two body samples, for example, using Northern blots and nucleotide probes. The level of mRNA expressed from of at least one member of the REG gene family or the gene represented by the Hs.11 1244 polynucleotide in a body sample of a human suspected of having chronic mucosal injury, can be compared with the mRNA expression from at least one member of the REG gene family or the gene represented by Hs.111244 polynucleotide in a healthy body sample. This can be done, for example, using in situ hybridization in tissue section or in Northern blots containing poly $A^+$mRNA. A higher level of mRNA expressed from a gene represented by a Hs.111244 polynucleotide in the suspect body sample as compared to the healthy body sample is indicative of ulcerative colitis in the suspect human who has provided the body sample. A higher level of mRNA expressed from a REG family gene in the suspect body sample as compared to the healthy body sample is indicative of chronic mucosal injury in the suspect human who has provided the body sample. Preferably, the increased level of mRNA expressed from a member of the REG gene family or the gene represented by the Hs.111244 polynucleotide in the suspect body sample is at least 25%, 50%, 100%, 150%, 200%, or 250% higher than in the healthy body sample.

If desired, the level of a particular mRNA, polypeptide, or protein expressed from a REG gene family member or mRNA expressed from a gene represented by a Hs.111244 polynucleotide in a body sample can be quantitated. Quantitation can be accomplished, for example, by comparing the level of expression product detected in the body sample with the level of expression product present in a standard curve. A comparison can be made visually or using a technique such as densitometry, with or without computerized assistance.

In a preferred embodiment, chronic mucosal injury can be differentiated from common acute inflammatory colon disorder and common non-inflammatory benign colon disorder in a human with symptoms of bowel disease. The amount of at least one gene expression product such as nRNA or protein of the REG gene family in the suspect body sample is compared to the amount of the same gene expression product in a body sample of a human which is healthy. The gene expression products in the two samples can be compared by any means known in the art. A body sample from a human suspected of having bowel disease which contains more of the gene expression product than the body sample of the healthy human identifies the suspect human as having chronic mucosal injury. Preferably the amount of the gene expression product in the body sample of the human with chronic mucosal injury is increased by at least 25%, 50%, 75%, 100%, 200%, or 250%.

Further, ulcerative colitis can be differentiated from common acute inflammatory colon disorder, common non-inflammatory benign colon disorder, and Crohn's disease in a human with symptoms of bowel disease. The amount of mRNA which is expressed by a gene represented by a Hs.111244 polynucleotide in a first body sample of a human suspected of having bowel disease is compared with the amount of the mRNA in a body sample of a second human which is healthy. The amount of mRNA in the two samples can be compared by any means known in the art. A body sample from a human suspected of having bowel disease which contains more of the mRNA than the body sample of the healthy human identifies the suspect human as having ulcerative colitis. Preferably the amount of mRNA in the body sample of the human with ulcerative colitis is increased by at least 25%, 50%, 75%, 100%, 200%, or 250%.

The degree of injury to the small intestine or colon tissue of a human with chronic mucosal injury can be determined by measuring the quantity of a gene expression product, such as mRNA or protein, of the REG gene family in a body sample of the human. The quantity of the gene expression product is correlated with the degree of injury to the small intestine or colon.

Further the degree of injury to the colon tissue of a human with ulcerative colitis can be determined by measuring the quantity of a mRNA which is expressed by a Hs.111244 polynucleotide or the gene represented by it in a body sample of the human. The quantity of the mRNA is correlated with the degree of injury to the colon.

The efficacy of therapy for chronic mucosal injury can be monitored in a body sample of a human with chronic mucosal injury. At least one gene expression product of the REG gene family can be quantitated in a body sample of a human which has been subjected to therapy for chronic mucosal injury. The quantity of the gene expression product in a matched body sample is compared to the quantity of the gene expression product in the body sample at an earlier time. A reduction of in the quantity of the gene expression product after therapy is an index of efficacy of the therapy. Preferably, the amount of the gene expression product is decreased by at least 10%, 25%, 50%, 75% or 100%.

The efficacy of therapy for ulcerative colitis in a human body sample can also be monitored. An mRNA which is expressed by a Hs.111244 polynucleotide or the gene represented by it is quantitated in a body sample of a human which has been subjected to therapy for ulcerative colitis. The quantity of the mRNA in the sample is compared to the quantity of the mRNA in the matched body sample at an earlier time. A reduction of in the quantity of the mRNA after therapy is an index of efficacy of the therapy. Preferably, the amount of the mRNA is decreased by at least 10%, 25%, 50%, 75% or 100%.

According to another aspect of the invention, compounds which have anti-chronic mucosal injury or anti-ulcerative colitis activity can be identified. A colonic cell expressing a gene of the REG family or a gene represented by the Hs.1 11244 polynucleotide can be contacted with a test compound. The test compound can be a pharmacologic agent already known in the art or can be a compound previously unknown to have any pharmacological activity. The test compound can be naturally occurring or designed in the laboratory. It can be isolated from microorganisms, animals, or plants, and can be produced recombinantly, or synthesized by chemical methods known in the art.

The cell can be any primary human cell or human cell line which expresses a REG family gene, or a gene represented by the Hs.111244 polynucleotide, as disclosed above. Methods of establishing cultures of primary human cells or of culturing cell lines are well known in the art.

Expression of at least one gene of the REG gene family or the gene represented by the Hs.111244 polynucleotide can be monitored. Expression can be measured in a sample of the same cell population before and after contact with the test compound. Alternatively, control cell populations can be employed. A test compound which decreases expression of at least one member of the REG gene family is identified as a potential drug for chronic mucosal injury. A test compound which decreases expression of a gene represented by the Hs.111244 polynucleotide is identified as a potential drug for decreasing ulcerative colitis. Preferably, the test compound decreases the amount of the gene expression product by at least 10%, 25%, 50%, 75% or 100%.

SEQUENCE LISTING

SEQ ID NO:1 cDNA sequence of pancreatic stone protein (PSP)
SEQ ID NO:2 cDNA sequence of pancreatitis-associatedprotein (PAP)
SEQ ID NO:3 cDNA sequence of human pancreatic beta cell growth factor (INGAP)
SEQ ID NO:4 cDNA sequence of regenerating gene homologue (REGH)
SEQ ID NO:5 cDNA sequence of Hs.11124

EXAMPLE 1

PSP, PAP and REGH are expressed in colonic mucosa of patients with inflammatory bowel disease. Parallel methods of measuring gene expression have been recently developed which allow concurrent measurement of the expression of a large number of genes. Light-directed solid-phase combinatorial chemistry was used to generate oligonucleotide probe arrays which provide representation of nearly 7000 human cDNA and EST sequences. Each gene is represented by 20 individual 25-mer oligonucleotide sequences. mRNA isolated from the mucosa of colonic resection specimens was used to generate hybridization probes for our analysis. Details of the GENECHIP technology, probe synthesis, hybridization, and confocal scanning have been previously described. The fluorescence intensity for different levels of gene expression was standardized by spiking known amounts of control genes into the probe mixture (FIG. 1). Detection at 1.5 pM is approximately equal to one message copy per cell. Tissue samples taken from the area used to isolate RNA were sent for histochemistry to be scored for acute and chronic inflammation, ulceration, dysplasia, eosinophilia, epithelial apoptosis, and metaplastic changes. Expression levels of PSP, PAP, and REGH in 15 clinical specimens are shown in FIG. 2. PSP RNA expression was in the top 2% of all arrayed genes in ulcerative colitis. Expression levels corresponded closely to histologic measures of disease activity. One non-IBD patient with severe acute inflammation, but no ulceration (rectal prolapse-specimen 11), did not express detectable PSP, PAP, or REGH.

EXAMPLE 2

Figure 3:
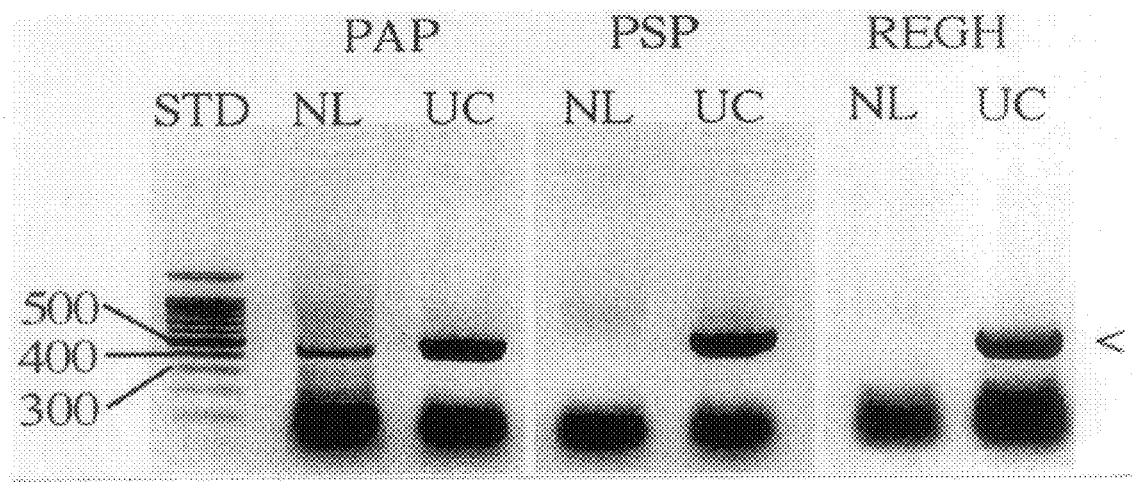
FIG. 3 demonstrates the use of reverse transcriptase PCR with primers specific for PAP, PSP, or REGH on mRNA isolated from a healthy human and a human with ulcerative colitis.

*Pichia pastoris* expression vectors were constructed with PSP, PAP, and REGH. Gene-specific primer pairs were designed to incorporate a 5' Xho I site, and a portion of the α-factor gene leading up to the yeast Ste13 cleavage site (5' end) and a Xba I containing primer that deleted the stop codon and included a 3' Myc epitope tag. After Kex2 and Ste13 signal cleavage by Pichia, the amino-terminus should be identical to the native secreted protein. RT-PCR was performed using the TITAN One Tube System (Boehringer Mannheim). The PCR products of these reactions, using RNA from a healthy or UC patient are shown in FIG. 3. These results demonstrate trace amounts of PAP in the "normal" patient examined, but otherwise agree with the results of the GENECHIP hybridization. Bands were gel purified and cloned into pGEM-T (Promega). The Xba/Xho gene fragments were excised and ligated into pPICZ( (Invitrogen). Constructs were bidirectionally sequenced with primers derived from the vector and were found to match the published sequences. Linearized plasmids were transformed into Pichia KM71 and recombinant clones identified by Zeocin selection.

EXAMPLE 3

PSP, PAP, and REGH were expressed in *Pichia pastoris*. PICZα places the inserted gene downstream of a strong methanol-inducible AOX1 promoter. Individual clones were grown in 10 ml cultures of BMGY media overnight and resuspended into ⅕ volume of BMMY (0.5% methanol) for induction. Aliquots of media supernatant were taken at various times after methanol induction and subjected to 15% SDS-PAGE. PSP or REGH expression was identified by the new appearance of 18 and 18.5 kDa bands (respectively), peaking 48 hours after induction. These sizes include the 2.5 kDa C-terminal epitope tag, whose presence was verified by Western blot (ECL) utilizing a monoclonal anti-Myc antibody (Invitrogen). Tryptic digestion of both PSP and REGH led to a mobility reduction of about 1 kDa, reflecting the expected size change following cleavage at the Arg11-Ile12 bond (data not shown). PAP expression was also demonstrated.

Figure 4:
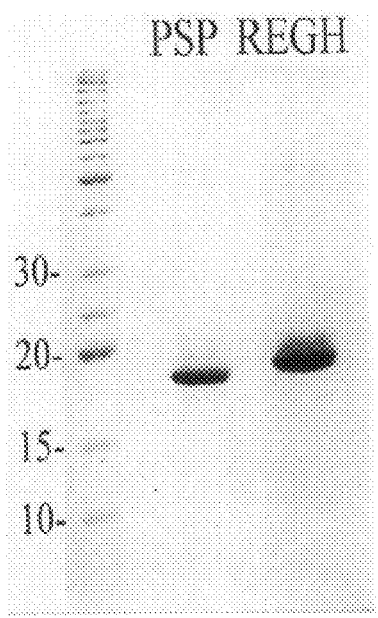
FIG. 4 demonstrates the purification of recombinant PSP and REGH proteins.

Large scale protein purification was performed by directly scaling up the protocol outlined above. Pichia from 1.5 liter cultures were resuspended into 300 mls of BMMY induction media and allowed to grow for 48 hours. Culture supernatants were concentrated by ammonium sulfate precipitation and column purified by Bio-Gel P30. Fractions containing PSP or REGH were pooled and concentrated using a Centriprep 10 concentrator (Amicon). FIG. 4 shows a Coomassie-stained SDS-PAGE gel of the purified proteins.

What is claimed is:

1. A method of screening for chronic inflammatory bowel disease comprising:

detecting at least one gene expression product of the regenerating (REG) gene family in a colon sample of a first human, wherein the first human is suspected of having chronic inflammatory bowel disease, wherein the expression product is an mRNA of a gene selected from the group consisting of pancreatitis-associated protein (PAP), and regenerating gene homologue (REGH);

identifying the first human as having an increased risk of having chronic inflammatory bowel disease if the gene expression product is detected.

2. The method of claim 1 wherein an amount of the gene expression product detected in the colon sample of the first human is compared with an amount of the gene expression product detected in a colon sample of a second human, wherein the second human is healthy, wherein more of the gene expression product detected in the colon sample of the first human than in the colon sample of the second healthy human, confirms chronic inflammatory bowel disease in the first human.

3. The method of claim 1 wherein an assay selected from the group consisting of Northern blot assay, DNA array, and ribonuclease protection assay, is used to detect the mRNA.

4. The method of claim 1 wherein the expression product is an mRNA of pancreatitis-associated protein (PAP).

5. The method of claim 1 wherein the expression product is an mRNA of regenerating gene homologue (REGH).

6. The method of claim 1 wherein the chronic inflammatory bowel disease is ulcerative colitis.

7. The method of claim 1 wherein the chronic inflammatory bowel disease is Crohn's disease.

* * * * *